United States Patent [19]

Cornwall et al.

[11] Patent Number: 4,586,518

[45] Date of Patent: May 6, 1986

[54] HAIR SETTING METHOD USING AMINOALKYL SUBSTITUTED POLYDIORGANOSILOXANE

[75] Inventors: Susan M. Cornwall; Gary R. Homan, both of Midland, Mich.

[73] Assignee: Dow Corning Corporation, Midland, Mich.

[21] Appl. No.: 637,992

[22] Filed: Aug. 6, 1984

[51] Int. Cl.$^4$ .............................................. A45D 7/00
[52] U.S. Cl. ........................................... 132/7; 424/70
[58] Field of Search ............................... 132/7; 424/70

[56] References Cited

U.S. PATENT DOCUMENTS

| | | | |
|---|---|---|---|
| 2,643,375 | 6/1953 | Gant | 132/7 |
| 2,750,947 | 6/1956 | Gant | 132/7 |
| 2,782,790 | 2/1957 | Hersh et al. | 132/7 |
| 2,787,274 | 4/1957 | Gant et al. | 132/7 |
| 2,840,087 | 6/1958 | Hersh | 132/7 |
| 3,248,296 | 4/1966 | Steinbach et al. | 167/87 |
| 4,344,763 | 8/1982 | Tolgyesi et al. | 8/127.51 |

OTHER PUBLICATIONS

Sardo, "New Types of Hair Setting Sprays Having Semipermanent Properties", pp. 43, 44, 46, Dec. 1972, *American Cosmetics and Perfumery*, vol. 87.

*Primary Examiner*—Gregory E. McNeill
*Attorney, Agent, or Firm*—James E. Bittell

[57] ABSTRACT

The specification describes a hair setting method that employs a hair fixative composition containing an aminoalkyl substituted polydiorganosiloxane as the effective component. The hair fixative composition may be formulated into aerosol, pump spray, lotion, cream or mousse type compositions for easy application to hair. The aminoalkyl substituted polydiorganosiloxane improves the curl retention of the hair after setting and provides conditioning to the hair.

10 Claims, No Drawings

HAIR SETTING METHOD USING AMINOALKYL SUBSTITUTED POLYDIORGANOSILOXANE

BACKGROUND OF THE INVENTION

This invention relates to a method of setting hair which produces hair that retains, for an extended period, a desired configuration imposed on it by means of curlers, pins or other hair styling vehicles. More specifically, the invention relates to a method of setting hair employing a hair setting composition containing as an effective component an aminoalkyl substituted polydiorganosiloxane.

Many popular hair styles require a means to hold the hair in a desired configuration. Several procedures are commonly used for setting hair styles at home and in beauty salons including, for example, the winding of wetted hair around curlers or rods followed by drying; the winding of moist hair around a hot curling iron; and the blow drying of wet hair while rolling the hair around a hand held brush. It is generally recognized that the physical and chemical action of water plays a significant role in the process of setting hair. When hair is wetted, hydrogen bonds in the keratin of hair are broken. Then when hair is shaped using curlers, irons, or brush and dried, hydrogen bonds are reformed at locations different from the previous ones and the hair style is thus set.

When hair is set by the use of water alone, the hair style gradually loses its shape through the absorption of atmospheric moisture and consequent rearrangement of the hydrogen bonds. A considerable number of hair setting compositions have been suggested to facilitate the setting of hair styles and especially to extend the time period that the set is retained in the hair. Such compositions range from the permanent wave types which operate chemically by breaking and reforming disulfide linkages in the hair protein to preparations which leave a thin layer of film-forming resin on the hair which when dried tends to mechanically maintain the hair in the shape of the dried resin film. Generally, the filmforming resin preparations have been composed of water or alcohol solutions of anionic polymers such as polyvinylpyrrolidone, polyvinylpyrrolidone-vinylacetate copolymers, polymethacrylate resins, ethyl and butyl monoesters of polymethylvinyl ether and maleic acid, or carboxylated polyvinylacetate copolymers.

While the film-forming resin preparations do improve the length of set retention in hair, it has generally been found that the stiff resin film tends to make the hair objectionably sticky and to produce flaky or linty particles on the hair as the film breaks up during combing or brushing. Moreover, because of the hydrophilic nature of the resins, they are removed from the hair with each shampooing and must be continually reapplied to be effective. The sticky character of the resin films also makes the coated hair difficult to comb or brush and may result in damaging or breaking hairs during such operations.

On the other hand, organic cationic compounds and polymers such as stearyldimethylbenzylammonium chloride, quaternary nitrogen derivatives of cellulose ethers, and homopolymers and copolymers of dimethyldiallylammonium chloride are well known for use in hair conditioning formulations. Hair conditioners facilitate combing out hair and impart softness and suppleness to the hair. Cationic polymers are further known in the art for their substantivity which enables them to become fixed to hair and to remain on hair. However, the conventional cationics generally show little or no effect in facilitating the setting of hair styles or providing retention of hair sets over extended periods.

Accordingly, it is a purpose of the present invention to provide an improved method of setting hair using a hair fixative composition that conditions the hair; is substantive and fixed to the hair; facilitates the setting of hair styles; increases the length of time that the set is retained in the hair; and does not make the hair feel unnaturally sticky or stiff.

It is taught in U.S. Pat. Nos. 2,643,375 and 2,750,947 to treat hair with a thermosettable organosilicon resin which is then heat cured while positioning the hair in a desired arrangement. In a related vein, it's taught in U.S. Pat. Nos. 2,782,790, 2,787,274, and 2,840,087 to treat hair with a hydrolyzed or hydrolyzable alkoxyorganosilane solution which by silanol condensation forms a cured resin layer on the hair and physically holds a set in the hair. To obtain a more convenient cure, it is taught in an article entitled "New Types of Hair Setting Sprays having Semi-Permanent Properties" authored by Fulvio Sardo in Volume 87, *American Cosmetics and Perfumery*, pages 43–46 (December 1972), to employ a mixture of silanol endblocked dimethylpolysiloxane and a tetraalkyltitanate. This mixture cures by reaction with water when applied to the hair.

In U.S. Pat. No. 4,344,763, Tolgyesi et al. teaches a method of setting hair using a setting composition containing aminoalkyltrialkoxysilane and tetraalkyltitanante. When the composition is applied to wet hair, the alkoxysilane groups hydrolyze forming reactive silanol intermediates which condense in combination with the titanate. The resulting titanate cured siloxane coating is said to provide high set holding capability even at high humidity.

U.S. application for patent, Ser. No. 536,042, filing date Sept. 26, 1983, teaches a method of setting hair using a setting composition containing an aminoalkyl substituted polydimethylsiloxane and tetraalkyltitanates. The siloxane does not contain silanol or potential silanol functionality so that it cannot cure by the silanol condensation reaction utilized in earlier compositions. Instead it is believed to cure by an interaction of the titanate with the amino groups of the siloxane polymer. The cured composition is said to maintain a set in hair even when exposed to high atmospheric humidity but upon direct contact with water the interaction of amine and titanate is broken down and the set is thus removed from the hair.

U.S. application for patent, Ser. No. 595,224, filing date Mar. 30, 1984, teaches that an emulsion containing an aminoalkyl substituted polydimethylsiloxane is useful as a hair conditioner because it facilitates combing and imparts a smooth feel to hair. This application does not teach or suggest that the emulsion of aminoalkyl substituted polydimethylsiloxane could be used in a method of setting hair to increase the length of time a set is retained in hair.

It is taught in U.S. Pat. No. 3,248,296 to treat hair with an epoxidized organosiloxane after the hair has undergone a permanent wave treatment (rearrangement of disulfide bonds). The siloxane treated hair is said to retain its shape under more severe conditions than permanent waved but untreated hair.

SUMMARY OF THE INVENTION

The present invention relates to a method of setting hair comprising the steps of (A) rolling hair around a shaping device, (B) moistening the hair with water, (C) applying to the hair an effective amount of a fixative composition consisting essentially of 0.1 to 40 percent by weight of aminoalkyl substituted polydiorganosiloxane generally conforming to the formula

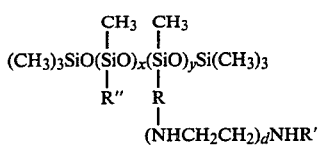

wherein R denotes an alkylene radical of 3 to 5 carbon atoms; R' denotes a hydrogen atom or an alkyl radical of 1 to 6 carbon atoms; each R" denotes a monovalent radical selected independently from the group consisting of methyl, ethyl, propyl, isopropyl, butyl, isobutyl, and phenyl; d has a value of 0, 1, 2, or 3; $x+y$ has an average value from 50 to 1000 and the ratio of y to x has a value from 0.02 to 0.15; the aminoalkyl substituted polydiorganosiloxane being carried in an aqueous emulsion or a physiologically acceptable organic solvent, and (D) drying the hair while the hair is rolled.

The steps of the method of setting hair may be performed in any order or simultaneously with the only exception being that the hair is dried while the hair is rolled and, of course, after the hair has been moistened with water.

DETAILED DESCRIPTION OF THE INVENTION

This invention is based on the discovery that one can improve the setting of hair styles and extend the period that the set is retained in hair by treating the hair with a fixative composition containing, as the active ingredient, a liquid, aminoalkyl substituted polydiorganosiloxane without any added curing component for the siloxane liquid. Surprisingly, the presence of the liquid siloxane on the hair not only provides conditioning benefits such as easy combing and smooth silky feel, but also provides excellent set holding benefits when the hair is set by the method of the present invention.

The precise nature of this set holding action is not completely understood, but it is believed that the amino groups of the siloxane may interact with atmospheric carbon dioxide to gel or cure the liquid siloxane to an immobile film on the hair surface. The thin layer of siloxane on the hair surface then tends to maintain the hair in the shape in which the siloxane was gelled or cured, resisting the tendency of the hair to revert to prior configurations. The cure of the siloxane is easily reversed, when a new hair style is desired, by washing the hair with water which breaks down the ammonium carbonate salt linkages and converts the siloxane film back to a more free-flowing liquid state. After washing, much of the siloxane polymer remains on the hair because of the substantive nature of the amino substituted polymer for the hair. Consequently, the siloxane continues to provide set holding benefits when the hair is again set in a new style.

The above theory is offered only as a possible explanation and is not intended to further limit or define the present invention. It is recognized that other mechanisms may contribute to the set holding benefits of the present invention. For example, the layer of siloxane on the hair surface may provide a hydrophobic barrier that reduces the rate of absorption of atmospheric moisture and thus reduces the rate of hydrogen bond rearrangement and loss of set in the hair.

The aminoalkyl substituted polydiorganosiloxane used in the present invention conforms generally to the formula

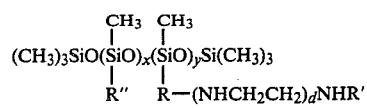

wherein R denotes an alkylene radical of 3 to 5 carbon atoms, R' denotes a hydrogen atom or an alkyl radical of 1 to 6 carbon atoms, and each R" denotes a monovalent radical selected independently from the group consisting of methyl, ethyl, propyl, isopropyl, butyl, isobutyl, and phenyl. The alkylene radicals denoted by R may include, for example, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CHCH$_3$CH$_2$—, and —CH$_2$CH$_2$CHCH$_3$CH$_2$—. However, siloxanes wherein R is a propylene or an alkyl substituted propylene radical, such as —CH$_2$CHCH$_3$CH$_2$—, are preferred because of ease of synthesis and availability. The alkyl radicals which may be denoted by R' include, among others, methyl, ethyl, propyl, butyl, isobutyl, hexyl, isopropyl, and isopentyl.

The monovalent radicals denoted by R" are each individually selected from the group consisting of methyl, ethyl, propyl, isopropyl, butyl, isobutyl, and phenyl so that the polydiorganosiloxane may contain, for example, dimethylsiloxane units, methylpropylsiloxane units, methylphenylsiloxane units, ethylmethylsiloxane units, isopropylmethylsiloxane units, butylmethylsiloxane units, isobutylmethylsiloxane units or any combination of these siloxane units. However, siloxanes wherein R" denotes methyl are preferred because of the ease of synthesis and availability of the dimethylsiloxane units.

The aminoalkyl substituent of the siloxane may contain from one to four nitrogen atoms such that d in the above formula has the value of 0, 1, 2, or 3. It has been found that nitrogen in the substituent must be in the form of primary or secondary amine functionality to provide improvement in curl retention by the method of this invention. For example, polydimethylsiloxane polymers bearing substituents containing nitrogen only in the form of amide or tertiary amine functionality do not provide any significant improvement in curl retention when used in the hair setting method of this invention.

The aminoalkyl substituted polydiorganosiloxanes useful in the present invention contain sufficient siloxane units so that the average value of $x+y$ in the above formula is within the range of about 50 to 1000. The siloxane is further characterized by the ratio of y to x which has a value from 0.02 to about 0.15. Siloxanes with a ratio of y to x of less than 0.02 may provide some conditioning benefits on hair but are less substantive to the hair and less durable on the hair. Because of their low level of amine functionality, such siloxanes provide very little, if any, set holding improvement to hair. It has been found that increasing the ratio of y to x in the siloxane polymers generally increases the set holding improvement that is obtained by the method of this invention. Consequently, it is preferred to use a siloxane polymer in which the ratio of y to x is 0.04 or above.

On the other hand, when the ratio of y to x is greater than about 0.15, it has been found that the siloxane imparts a greasy feeling to hair. Since a greasy feeling is generally considered undesirable, siloxanes with y to x ratios greater than 0.15 are not contemplated for this invention. Furthermore, to minimize any greasy feeling imparted to the hair by the method of this invention, it is preferred to employ a siloxane having a ratio of y to x below about 0.08.

Methods for preparing the aminoalkyl substituted polydiorganosiloxane polymers that are employed in the fixative composition according to this invention are well known in the art. For example, known polydiorganosiloxane polymers bearing reactive groups such as $\equiv$SiH or $\equiv$SiCH$_2$CH$_2$Cl may be reacted with CH$_2$$\equiv$C(CH$_3$)CH$_2$NH$_2$CH$_2$CH$_2$NH$_2$ or ethylenediamine, respectively, to provide suitable siloxanes. Alternatively, suitable aminoalkyl substituted polydiorganosiloxanes may be prepared from aminoalkyl substituted silanes or siloxanes using well known methods of hydrolysis and equilibration. It is usually preferred, for example, to prepare aminoalkyl substituted polydimethylsiloxanes by hydrolyzing a silane such as H$_2$NCH$_2$CH$_2$NHCH$_2$CHCH$_3$CH$_2$Si(CH$_3$)(OCH$_3$)$_2$ in excess water and equilibrating the resulting hydrolyzate with dimethylcyclopolysiloxane and decamethyltetrasiloxane using a base catalyst such as KOH.

The hair fixative composition according to the invention is prepared by dissolving the siloxane polymer in a physiologically acceptable organic solvent or by forming an aqueous emulsion of the siloxane polymer. Suitable organic solvents include, among others, the chlorinated alkanes such as 1,1,1-trichloroethane and methylene dichloride, and alcohols such as ethyl alcohol, isopropyl alcohol, and polyols such as ethylene glycol and propylene glycol. The siloxane polymer can also be employed in the fixative composition as an aqueous emulsion or dispersion. Aqueous emulsions or dispersions of the siloxane polymer may be prepared by high shear mixing the siloxane in water using a suitable emulsifying agent as is well known in the art. For example, the emulsification of aminoalkyl substituted polydimethylsiloxane polymers is described in U.S. Pat. No. 4,247,592 which is hereby incorporated by reference.

The amount of the aminoalkyl substituted polydiorganosiloxane in the hair fixative composition is in the range of 0.1 to 40 percent by weight, preferably 0.2 to 10 percent by weight, of the total composition. Lesser amounts result in very minimal improvements in set holding whereas larger amounts are inefficient and may produce a greasy feeling on the hair from over treatment.

The hair fixative composition may also contain other nonessential components such as thickeners, perfumes, colorants, propellant gases, organic cationic hair conditioners and carboxylic or mineral acids. When the fixative composition is intended to be applied to the hair by first placing a portion in the hand and then transferring to the hair, it is preferred that the fixative compositions also contain a thickener. The thickeners which can be used include sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose and starch amylose and locust bean gum. In nonaqueous systems, hydrophobic thickeners such as polyvinylethyl ether and polyvinylisobutyl ether can be used.

The concentration of thickeners when used is generally from 0.5 to 30 percent, and preferably from 0.5 to 15 percent, by weight.

The perfumes which can be used in the fixative compositions are the cosmetically acceptable perfumes and they may be present in amounts which vary from 0.1 to 0.5% by weight.

The colorants which are intended to confer a color to the compositions may generally be present in an amount from 0.001 to 0.5 percent by weight.

When the fixative composition is intended for aerosol application, propellant gases can be included such as carbon dioxide, nitrogen, nitrous oxide, volatile hydrocarbons such as butane, isobutane or propane and chlorinated or fluorinated hydrocarbons such as dichlorodifluoromethane and dichlorotetrafluoroethane.

The fixative composition used in the method of the present invention may also contain an organic cationic hair conditioning component. Organic cationic hair conditioning components are quaternary nitrogen containing organic compounds or polymers. The cationic compounds useful as hair conditioning components are generally cationic surface-active agents containing a saturated or unsaturated, linear or branched alkyl radical of 8 to 22 carbon atoms attached to cationic nitrogen. Cationic hair conditioning compounds include, among others, stearyldimethylbenzylammonium chloride or bromide, lauryltrimethylammonium chloride or bromide, dodecyldimethylhydroxyethylammonium chloride or bromide, dimethyldistearylammonium chloride or bromide and dimethyldilaurylammonium chloride or bromide.

Cationic organic polymers are well known in the art for their substantivity to hair and are used to facilitate combing out of the hair and impart to the hair softness and suppleness. Among the cationic organic polymers which can be used in the fixative compositions of the present invention, the following may be mentioned as examples: quaternary nitrogen derivatives of cellulose ethers, homopolymers of dimethyldiallylammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-$\alpha$,$\omega$-bis-(triethanolammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers.

The fixative composition used in the method of the present invention may also contain an organic carboxylic or polycarboxylic acid or a mineral acid such as hydrochloric, sulfuric or phosphoric acid to modify the pH of the composition. It has also been found, surprisingly, that the presence of an acid in the fixative composition reduces any greasy feeling imparted to hair by the aminoalkyl functional siloxane polymer. If an acid is used for this purpose, it is preferred to use a carboxylic or polycarboxylic acid. The amount of carboxylic acid or polycarboxylic acid that may be used in the fixative composition varies from about 0.01 to 10 percent by weight. Generally if a carboxylic acid is employed, it is preferred to use an amount sufficient to provide a pH in the range of 6 to 8 for the hair fixative composition.

Carboxylic acids that can be employed in the hair fixative compositions of this invention include, for example, monocarboxylic acids such as acetic acid, lactic acid, or propionic acid and polycarboxylic acids such as succinic acid, adipic acid and citric acid. Generally the only requirement in regard to the organic carboxylic acid is that the acid is soluble or readily dispersible in the carrier used for delivery of the amino functional polydiorganosiloxane polymer to the hair.

The hair fixative composition may be formulated by conventional means into aerosol, pump spray, lotion, cream or mousse type compositions for easy application to hair.

The steps of the method of this invention may be performed in any order or simultaneously with the only exception being that the hair is dried while the hair is rolled and, of course, after the hair has been moistened with water.

In the method of this invention, a desired shape or configuration is imposed on the hair by rolling the hair around a shaping device. Any of the conventional devices commonly used for setting hair styles may be employed in the method of this invention. For example the hair may be rolled on curlers, a curling iron or a hand held brush. The hair may be rolled while wet such as after shampooing or it may be rolled while dry and then moistened with water. Moistening of dry rolled hair may also be accomplished simultaneously with the application of the fixative composition when the fixative composition is applied in the form of an aqueous emulsion.

In the method of this invention, the fixative composition may be applied to the surface of the hair in any suitable manner such as by massaging the composition throughout the hair by hand, by dipping the hair into the composition, by brushing or combing the composition through the hair, by spraying the hair, or by padding the hair with sponges or cloth containing absorbed fixative composition. The fixative composition may be applied either before the hair is rolled or after it is rolled. Generally, however, it is preferred to apply the fixative composition prior to rolling the hair since it is easier to treat the hair evenly at this stage.

After the fixative composition is applied, the hair may or may not be rinsed with water. One of the surprising results of the instant invention is that even if the hair is rinsed after application of the fixative composition, the method of this invention still provides significantly improved curl retention in comparison to setting the hair with water only. The ability to rinse after application is an advantage of the present invention since it allows the use of components such as thickeners in the fixative composition which aid in the easy application of the composition to the hair, but which are not intended to be left or retained on the hair. Such components can be rinsed off while leaving the substantive aminoalkyl substituted polydiorganosiloxane polymer component on the surface of the hair where it provides curl retention.

Generally the amount of fixative composition is applied that is effective to provide an improvement in curl retention. The amount required will vary with the quantity and type of hair of each individual. Also the amount applied will vary depending on the extent of curl retention desired. Appropriate amounts for any individual's hair are readily determined by one or two trial applications.

The hair is dried while it is rolled in the desired shape or configuration. The hair may be dried by any convenient method such as by heating the hair with a blow dryer, with hot curlers, or with a heated curling iron. The hair may also be allowed to dry naturally at room temperature.

The method of this invention is further illustrated by the following examples which teach the best mode for carrying out the invention; however, the examples should not be regarded as limiting the invention which is delineated by the appended claims. All parts and percentages are by weight unless otherwise stated.

EXAMPLE 1

This example presents a method of setting hair of the present invention and illustrates the significant and reproducible improvement in curl after combing that is produced by the method.

Four stock emulsions containing aminoalkyl substituted polydimethylsiloxane generally conforming to the average formula

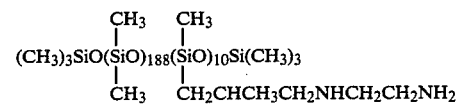

were prepared by high shear mixing 35 parts by weight of the siloxane, 3.5 parts by weight of octophenyl-40-ethyloxylate, 0.9 parts by weight of octophenyl-10-ethyloxylate and 60.6 parts water. Each stock emulsion represents a separate preparation of the aminoalkyl substituted polydimethylsiloxane.

Hair treatment compositions were prepared by diluting the stock emulsions with water to 5 weight percent silicone solids. Three swatches of Virgin European natural brown hair (3–4 g each swatch, 12 inches long) were treated with compositions prepared from each stock emulsion. Each hair swatch was soaked for two minutes in its treatment bath (100 ml), and then dipped ten times each in two 200 ml distilled water rinses. The treated hair swatches were rolled on 11/16 inch O.D. curlers and dried in a 70° C. oven for a minimum of 1.5 hours. Three water-wetted but untreated hair swatches were also rolled on curlers and dried for comparison.

The curlers were removed and the hair swatches allowed to hang freely under ambient conditions (57.5–59.0% R.H., 75° F.) for about one hour. The hair was then combed through twice and the curl length measured. The percent curl improvement for each treated hair swatch was determined as 100 times the difference between the curl length of the treated swatch and the average curl length of the three untreated hair swatches divided by the length of the treated hair swatch.

The curl lengths were measured again 5 hours and 23 hours later. At each measurement, the percent curl improvements were calculated as related to the curl length of the untreated hair determined at the measurement time.

The percent curl improvements determined at the three different times were averaged for each tress and are presented in Table 1. The average percent curl improvement over all 12 treated hair swatches over the 24 hour period was 31 percent.

TABLE 1
AVERAGE PERCENT CURL IMPROVEMENTS FOR INDIVIDUAL HAIR SWATCHES OVER 24 HOURS

| Stock Emulsion | Hair Swatches | | |
|---|---|---|---|
| | 1st | 2nd | 3rd |
| 1 | 35.6 | 36.6 | 24.1 |
| 2 | 40.2 | 34.0 | 29.6 |
| 3 | 27.2 | 32.4 | 37.5 |
| 4 | 30.8 | 28.0 | 16.9 |

EXAMPLE 2

This example illustrates the use of a relatively low molecular weight siloxane polymer in the hair setting method of the present invention.

An emulsion containing aminoalkyl substituted polydimethylsiloxane generally conforming to the average formula

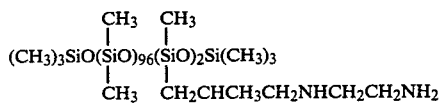

was prepared containing 35 parts of the siloxane, 3.6 parts octophenyl-40-ethyloxylate, 1.7 parts 2,6,8-trimethyl-4-nonyloxypolyethyleneoxyethanol, 1.4 parts ethylene glycol, and 58.3 parts water. A hair treatment bath was prepared by diluting 3.55 g of the above emulsion with 21.45 g water (5% silicone solids).

A swatch of 4 g Virgin European natural brown hair was soaked in the treatment bath for two minutes and then dipped ten times each in two distilled water baths. The treated tress and a water-wetted untreated tress were rolled on separate 11/16 inch O.D. curlers and dried in a 70° C. oven overnight. After drying, the curlers were removed and the tresses allowed to hang freely under ambient conditions (33–34% relative humidity, 74°–75° F.). After a half hour, the tresses were combed through twice and the curl length measured. Additional measurements were taken over an approximately 24 hour time interval. At each measurement, the percent curl improvement was calculated relative to the curl length of the untreated hair determined at the measurement time. The percent curl improvements at various times after removing the curlers and after combing are detailed in Table 2. The treated tress was also easier to comb and had a silkier feel than the untreated tress.

TABLE 2
PERCENT CURL IMPROVEMENT

| Elapsed Time from Uncurling (Hrs.) | Percent Curl Improvement |
|---|---|
| 0.5 | 34.6 |
| 6 | 25.0 |
| 22.5 | 25.7 |

EXAMPLE 3

This example presents a method of setting hair of the present invention and illustrates the improved curl retention that is produced by the method.

Two swatches of Virgin European natural brown hair (4 g, 12 inches long) were wetted with water and rolled on 11/16 inch O.D. curlers. The hair was dried on the curlers for two hours in a 70° C. oven. The curlers were then removed and each tress was combed twice. One tress was sprayed lightly with a solution of 10 weight percent aminoalkyl substituted polydimethylsiloxane in 1,1,1-trichloroethane. The siloxane conformed generally to the average formula

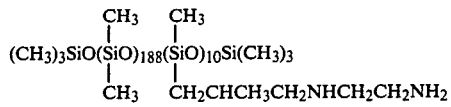

The other tress was left untreated for comparison.

Hair lengths were measured immediately after treatment and periodically afterward. Ambient temperature ranged from 69°–71° F. and relative humidity ranged from 50–57 percent during the test period. At each measurement, the percent curl improvement relative to the untreated tress was calculated as described in Example 1. The results are shown in Table 3. The curl was reduced initially by the spray treatment, possibly due to the weight of the add-on. However, when allowed to remain under ambient conditions for several hours, the treated tress surpassed the untreated tress for curl retention.

TABLE 3
CURL IMPROVEMENT WITH SPRAY TREATMENT

| Time of Measurement | Percent Curl Improvement |
|---|---|
| Before Spraying | 0 |
| Immediately After Spraying | −9 |
| 2 Hours After Spraying | 0 |
| 4 Hours After Spraying | 10 |
| 24 Hours After Spraying | 11 |
| 4 Days After Spraying | 22 |

EXAMPLE 4

This example illustrates the use of a quaternary nitrogen containing organic conditioner in combination with aminoalkyl substituted polydimethylsiloxane in the hair setting method of the present invention.

A stock emulsion containing aminoalkyl substituted polydimethylsiloxane generally conforming to the average formula

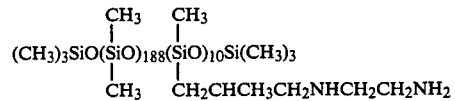

was prepared by high shear mixing 35 parts of the siloxane, 3.5 parts of octophenyl-40-ethyloxylate, 0.9 parts of octophenyl-10-ethyloxylate and 60.6 parts water. Three treatment compositions were prepared for comparison. Composition 1 was a 2 percent by weight aqueous solution of a quaternary nitrogen derivative of a cellulose ether (JR Resin ® 400, a well-known organic conditioner supplied by Union Carbide Corporation, New York, NY 10017). Composition 2 was a 2 percent siloxane solids emulsion prepared by diluting 2.86 g of the above stock emulsion with 47.14 g of water. Composition 3 was a mixture prepared by combining 1.42 g of the above siloxane stock emulsion, 0.5 g of the quaternary nitrogen derivative of cellulose ether, and 48.08 g water (1% siloxane, 1% organic conditioner).

A swatch of Virgin European natural brown hair (4 g, 12 inches long) was soaked for two minutes in each of the compositions and then rinsed in distilled water.

Each swatch was then rolled on a 11/16 inch O.D. curler and dried in a 70° C. oven for a minimum of 1.5 hours. A water-wetted but untreated hair swatch was also rolled on a curler and similarly dried as a control. The average curl improvements over a 24 hour period relative to the untreated control were determined as described in Example 1. In addition, each hair tress was evaluated for dry feel, body, and dry sheen. The results are presented in Table 4. While the organic conditioner was judged to improve the overall look and feel of the hair, it did not appear to enhance the curl retention of the hair.

TABLE 4

COMPARISON OF HAIR TREATMENTS

| Treating Composition | Average Curl Improvement | Dry Feel | Body | Dry Sheen |
|---|---|---|---|---|
| 1* | −4% | Very Slightly Raspy | Poor | Good |
| 2 | 41% | Slightly Greasy | Good | Fair |
| 3 | 18% | Very Slightly Raspy | Fair | Good |
| Control* | 0% | Very Good | Very Good | Very Good |

*Presented for comparison purposes, not within the scope of the present invention.

EXAMPLE 5

This example presents a method of setting hair of the present invention and illustrates the improved curl retention that is produced by the method.

Six swatches of Virgin European natural brown hair (3-4 g, 12 inches long) were hydrated by dipping ten times in a 100 g solution of 0.8 weight percent sodium laureth sulfate, $CH_3(CH_2)_{10}CH_2(OCH_2CH_2)_nOSO_3Na$ where n=1 to 4, in water and allowing them to soak for a total exposure of two minutes. The swatches were then rinsed by dipping them ten times in each of three 200 ml distilled water baths.

Three of the swatches were treated individually by dipping each swatch ten times in a treatment bath and allowing them to soak for a total exposure of two minutes. The treatment baths were 100 g of 5 percent silicone solids emulsions prepared by diluting the stock emulsion of aminoalkyl substituted polydimethylsiloxane described in Example 4. The three treated swatches were rinsed by dipping ten times each in two, 200 ml distilled water baths. The other three swatches were not treated and served as controls.

All six swatches were then individually dried with a hand held blow dryer to 110 percent of the swatch's dry weight while combing continually to facilitate moisture distribution. The treated swatches were found to be easier to comb and have a silkier feel than the untreated swatches. The swatches were then curled by rolling around a curling iron for one minute. The curl lengths were measured and the average curl improvement of the treated swatches relative to the untreated swatches were determined to be 7 percent. After combing through twice, the treated swatches averaged 8 percent curl improvement relative to the untreated swatches.

EXAMPLE 6

This example illustrates the use of organic carboxylic acids in combination with the aminoalkyl substituted polydimethylsiloxane in the hair setting method of the present invention.

Three hair treatment compositions were prepared employing the stock emulsion of aminoalkyl substituted polydimethylsiloxane described in Example 4. Composition I was prepared by diluting 15 g of stock emulsion with 135 g of water to provide a 3.5 weight percent silicone solids emulsion. Composition II was prepared by diluting 15 g of stock emulsion in 133.95 g water and then mixing in 1.05 g of succinic acid. Composition III was prepared by diluting 15 g of stock emulsion with 133.93 g water and then mixing in 1.07 g of acetic acid.

Eighteen swatches of Virgin European natural brown hair were hydrated as described in Example 5. Six swatches were individually treated in baths of Composition I and three swatches each were treated in Compositions II and III. The remaining six swatches were not treated and served as controls.

The hair swatches were rolled on 11/16 inch O.D. curlers and dried in a 70° C. oven for a minimum of 1.5 hours. After removing the curlers, the hair swatches were combed and allowed to hang freely under ambient conditions (22°-24° C., 37-41% R.H.). The percent curl improvement relative to the controls were determined immediately after initial unrolling and combing and also 2 hours and 24 hours later. The percent curl improvements determined at the three different times were averaged for all similarly treated swatches and are presented in Table 5.

The swatches treated with the silicone emulsion only were slightly dull in appearance. The acid-added treatments provided good sheen to the hair, although somewhat less curl improvement was observed.

TABLE 5

COMPARISON OF CURL IMPROVEMENTS FOR SILICONE AND ORGANIC ACID COMBINATIONS

| Hair Treatment | Average Percent Curl Improvement | Wet Comb | Wet Feel | Dry Appearance |
|---|---|---|---|---|
| I | 23 ± 10* | Very Easy | Silky But Tacky | Slightly Greasy |
| II | 14 ± 13* | Easy | Silky | Natural |
| III | 15 ± 1* | Easy | Silky | Natural |
| Control | 0 | Difficult | Raspy | Natural |

*Calculated variation for 90% confidence.

That which is claimed is:
1. A method of setting hair comprising the steps of:
(A) rolling the hair around a shaping device,
(B) moistening the hair with water,
(C) applying to the hair an effective amount of a fixative composition consisting essentially of 0.1 to 40 percent by weight of aminoalkyl substituted polydiorganosiloxane generally conforming to the formula

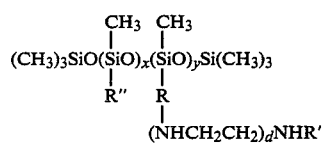

wherein R denotes an alkylene radical of 3 to 5 carbon atoms; R' denotes a hydrogen atom or an alkyl radical of 1 to 6 carbon atoms; each R" denotes a monovalent radical selected independently from the group consisting of methyl, ethyl, propyl, isopropyl, butyl, isobutyl, and phenyl; d has a value of 0, 1, 2, or 3; x+y has an average value from 50 to 1000 and the ratio of y to x has a value from 0.02 to 0.15; the aminoalkyl substituted polydiorganosiloxane being carried in an aqueous emulsion or a physiologically acceptable organic solvent, and (D) drying the hair while the hair is rolled.

2. The method according to claim 1 wherein R″ denotes a methyl radical.

3. The method according to claim 2 wherein the aminoalkyl substituted polydiorganosiloxane is carried in an organic solvent selected from the group consisting of chlorinated alkanes, alcohols and polyols.

4. The method according to claim 3 wherein the organic solvent is 1,1,1-trichloroethane.

5. The method according to claim 2 wherein the aminoalkyl substituted polydiorganosiloxane is carried in an aqueous emulsion.

6. The method according to claim 5 wherein the fixative composition consists essentially of 0.2 to 10 percent by weight of aminoalkyl substituted polydiorganosiloxane.

7. The method according to claim 6 wherein the ratio of y to x has a value from 0.04 to 0.08.

8. The method according to claim 7 wherein R denotes a propylene or an alkyl substituted propylene radical, R′ denotes a hydrogen atom, and d has a value of 1.

9. The method according to claim 8 wherein R denotes $-CH_2CHCH_3CH_2-$.

10. The method according to claim 7 wherein the fixative composition further contains a water soluble carboxylic or polycarboxylic acid in sufficient amount to provide a pH in the range of 6 to 8 for the hair fixative composition.

* * * * *

UNITED STATES PATENT AND TRADEMARK OFFICE
CERTIFICATE OF CORRECTION

PATENT NO. : 4,586,518
DATED     : May, 6, 1986
INVENTOR(S) : Susan M. Cornwall and Gary R. Homan It is certified that error appears in the above-identified patent and that said Letters Patent is hereby corrected as shown below:

In Column 5; Line 17 the formula "$\equiv SiCH_2CH_2Cl$" should read
-- $\equiv SiCH_2CH_2CH_2Cl$ --.

In Column 5; Line 18 the formula "$CH_2 \equiv C(CH_3)CH_2NH_2CH_2CH_2NH_2$" should read -- $CH_2 = C(CH_3)CH_2NH_2CH_2CH_2NH_2$ --.

Signed and Sealed this

Second Day of September 1986

[SEAL]

Attest:

DONALD J. QUIGG

Attesting Officer

Commissioner of Patents and Trademarks